United States Patent
Himmler

(10) Patent No.: US 8,669,372 B2
(45) Date of Patent: Mar. 11, 2014

(54) PROCESS FOR PREPARING DITHIINE-TETRACARBOXY-DIIMIDES

(75) Inventor: Thomas Himmler, Odenthal (DE)

(73) Assignee: Bayer CropScience AG, Monheim (DE)

( * ) Notice: Subject to any disclaimer, the term of this patent is extended or adjusted under 35 U.S.C. 154(b) by 225 days.

(21) Appl. No.: 13/086,506

(22) Filed: Apr. 14, 2011

(65) Prior Publication Data

US 2011/0257411 A1 Oct. 20, 2011

Related U.S. Application Data

(60) Provisional application No. 61/325,081, filed on Apr. 16, 2010.

(30) Foreign Application Priority Data

Apr. 14, 2010 (EP) .................................. 10159900

(51) Int. Cl.
*C07D 491/00* (2006.01)
*C07D 207/444* (2006.01)

(52) U.S. Cl.
USPC ........................... 548/431; 548/548; 548/549

(58) Field of Classification Search
None
See application file for complete search history.

(56) References Cited

U.S. PATENT DOCUMENTS 3,364,229 A * 1/1968 Korte et al. ................... 548/431
2010/0120884 A1 5/2010 Seitz et al.

FOREIGN PATENT DOCUMENTS

JP 10-251265 A 9/1998
PL 143 804 11/1988
WO WO 2010/043319 A1 4/2010

OTHER PUBLICATIONS

Draber, W., "Synthese von 1,4-Dithiinen aus Derivaten des Maleinimids," *Chem. Ber.* 100:1559-1570, Wiley-VCH, Germany (1967).
Unverified English translation of Draber, W., "Syntheses of 1,4-Dithiins from Maleimide Derivatives," *Chem. Ber.* 100:1559-1570, Deutsche Chemische Gesellschaft, Germany (1967).
Zentz, F., et al., "Syntheses, in vitro antibacterial and antifungal activities of a series of $N$-alkyl, 1,4-dithiines," *Il Farmaco* 60:944-947, Elsevier, France (2005).
Unverified English language of Polish Patent Application No. 143 804, Patent Office of the Polish People's Republic, Poland.
English language abstract for Japanese Patent Application No.: JP 10-251265 A, published Sep. 22, 1998, Japanese Patent Office, Espacenet database—Worldwide (1998).

* cited by examiner

*Primary Examiner* — Nyeemah A Grazier
(74) *Attorney, Agent, or Firm* — Sterne, Kessler, Goldstein & Fox P.L.L.C.

(57) ABSTRACT

The present invention relates to a new process for preparing dithiine-tetracarboxy-diimides.

10 Claims, No Drawings

PROCESS FOR PREPARING DITHIINE-TETRACARBOXY-DIIMIDES

The present invention relates to a new process for preparing dithiine-tetracarboxy-diimides.

Dithiine-tetracarboxy-diimides as such are already known. It is also known that these dithiine-tetracarboxy-diimides can be used as anthelmintics against internal parasites of animals, more particularly nematodes, and have insecticidal activity (cf. U.S. Pat. No. 3,364,229). It is known, furthermore, that certain dithiine-tetracarboxy-diimides possess antibacterial activity and have a certain activity against human mycoses (cf. Il Farmaco 2005, 60, 944-947). It is known, furthermore, that dithiine-tetracarboxy-diimides can be used as pigments in electrophotographic photoreceptors or as dyes in paints and polymers (cf. Jp-A 10-251265, PL-B 143804).

Dithiine-Tetracarboximides of the Formula (I)

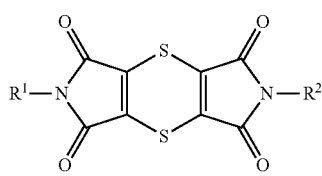

(I)

in which $R^1$ and $R^2$ are identical or different and are hydrogen, or are $C_1$-$C_8$-alkyl which is optionally substituted one or more times by halogen, —$OR^3$, and/or —$COR^4$, are $C_3$-$C_7$-cycloalkyl which is optionally substituted one or more times by halogen, $C_1$-$C_4$-alkyl or $C_1$-$C_4$-haloalkyl, or are aryl or aryl-($C_1$-$C_4$-alkyl) each of which is optionally substituted one or more times by halogen, $C_1$-$C_4$-alkyl, $C_1$-$C_4$-haloalkyl, —$COR^4$ or sulphonylamino, $R^3$ is hydrogen, $C_1$-$C_4$-alkyl or $C_1$-$C_4$-alkylcarbonyl or is aryl which is optionally substituted one or more times by halogen, $C_1$-$C_4$-alkyl or $C_1$-$C_4$-haloalkyl, $R^4$ is hydroxyl, $C_1$-$C_4$-alkyl or $C_1$-$C_4$-alkoxy, can be prepared in a variety of known ways.

For example, in one known process (cf. Synthetic Communications 2006, 36, 3591-3597), in a first stage, succinic anhydride is reacted with an amine of the formula (II), optionally in the presence of a diluent. Subsequently, the resultant succinic monoamides of the formula (III) are then reacted with a large excess of thionyl chloride in the presence of dioxane as diluent at room temperature, to give, finally, in a sequence of numerous reaction steps, the dithiine-tetracarboxy-diimides of the formula (I). The dithiine-tetracarboxy-diimides are optionally isolated directly from the reaction mixture or by filtration following addition of water. Depending on reaction conditions (diluents) and the nature of the radicals R, it is possible in certain circumstances to isolate the dithiine-diisoimides of the formula (IV) before they are converted into the dithiine-tetracarboxy-diimides of the formula (I):

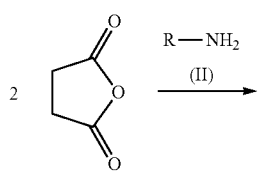

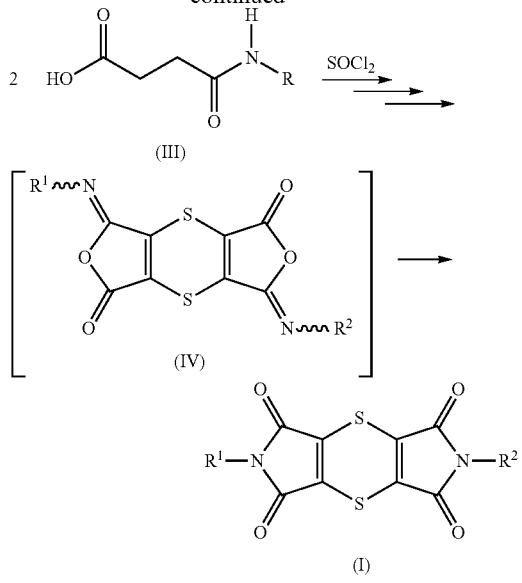

$R = R^1$ or $R^2$

Disadvantages of this process are the long reaction time and also the outcome where either the yields obtained generally do not exceed about 30-40% of theory or else the purities of the isolated products are inadequate. A further disadvantage, in the case of aqueous work-up of the reaction mixture, is that it involves destroying large amounts of thionyl chloride; the gases formed ($SO_2$ and HCl) have to be disposed of. Likewise a disadvantage is the fact that, from experience, the product is not obtained in one portion. Instead, it is frequently the case that, following initial isolation of product by filtration, further product precipitates from the filtrate after prolonged standing (overnight, for example), and must be isolated again by filtration. Occasionally this operation must be carried out once more. This procedure is very laborious and time-consuming.

In another known process (cf. U.S. Pat. No. 3,364,229; Chem. Ber. 1967, 100, 1559-70), in a first stage, dichloromaleic anhydride of the formula (V) is reacted with an amine of formula (II), optionally in the presence of a diluent. Subsequently, the resultant dichloromaleimides of the formula (VI) are then reacted with a sulphur donor compound (for example hydrogen sulphide, thiourea or sodium thiosulphate):

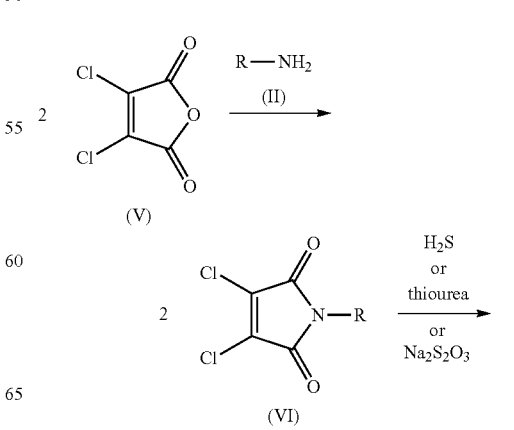

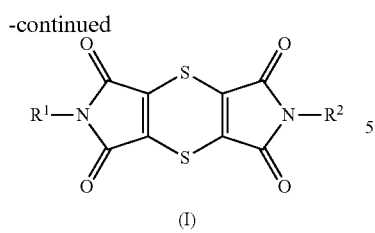

R = R¹ or R²

This process has the disadvantage that, for example, operating with the highly toxic gaseous hydrogen sulphide is from a technical standpoint very difficult, costly and inconvenient. When thiourea is used, unwanted by-products are obtained along with the target product, and are very difficult to remove and detract from the attainable yields. If sodium thiosulphate is used, the yield described is insufficient for an industrial operation.

Consequently there continues to be a need for a technically simple and economic preparation process for dithiine-tetracarboxy-diimides of the formula (I).

A new process has now been found for preparing dithiine-tetracarboxy-diimides of the general formula (I)

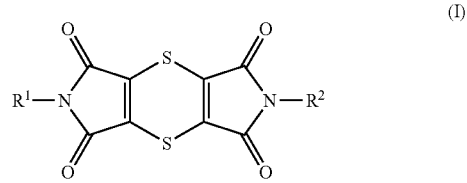

in which $R^1$ and $R^2$ have the definitions indicated above, characterized in that
dichloromaleimides of the formula (VI)

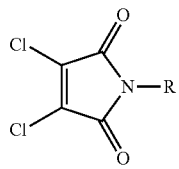

in which R is $R^1$ or $R^2$
are reacted with an inorganic thiopsulphate in a solvent or solvent mixture in a molar ratio between 1.1 and 1.8 mol of thiosulphate per mole of dichloromaleimide of the formula (VI).

A general definition of the dichloromaleimides used as starting materials when carrying out the process of the invention is provided by the formula (VI), R stands for the definitions of $R^1$ or $R^2$.

$R^1$ and $R^2$ are preferably identical or different and preferably are hydrogen, or are $C_1$-$C_6$-alkyl which is optionally substituted one or More times by fluorine, chlorine, bromine, —$OR^3$ and/or —$COR^4$, or are $C_3$-$C_7$cycloalkyl which is optionally substituted one or more times by chlorine, methyl or trifluoromethyl, or are phenyl or phenyl-($C_1$-$C_4$-alkyl) each of which is optionally substituted one or more times by fluorine, chlorine, bromine, methyl, trifluoromethyl, —$COR^4$ and/or sulphonylamino.

$R^1$ and $R^2$ are more preferably identical or different and more preferably are hydrogen, or are $C_1$-$C_4$-alkyl which is optionally substituted one or more times by fluorine, chlorine, hydroxyl, methoxy, ethoxy, methylcarbonyloxy and/or carboxyl, or are $C_3$-$C_7$-cycloalkyl which is optionally substituted one or more times by chlorine, methyl or trifluoromethyl; or are phenyl, benzyl, 1-phenethyl, 2-phenethyl or 2-methyl-2-phenethyl each of which is optionally substituted one to three times by fluorine, chlorine, bromine, methyl, trifluoromethyl, —$COR^4$ and/or sulphonylamino.

$R^1$ and $R^2$ are very preferably identical or different and very preferably are hydrogen, methyl, ethyl, n-propyl, isopropyl, 2,2-difluoroethyl or 2,2,2-trifluoroethyl or are cyclopropyl or cyclohexyl each of which is optionally substituted by chlorine, methyl or trifluoromethyl.

$R^1$ and $R^2$ are more particularly preferably simultaneously methyl.

$R^3$ is preferably hydrogen, methyl, ethyl, methylcarbonyl or ethylcarbonyl or is phenyl which is optionally substituted one or more times by fluorine, chlorine, methyl, ethyl, n-propyl, isopropyl or trifluoromethyl $R^3$ is more preferably hydrogen, methyl, methylcarbonyl phenyl.

$R^4$ preferably is hydroxyl, methyl, ethyl, methoxy or ethoxy.
$R^4$ is more preferably hydroxyl or methoxy.

As starting material it is particularly preferred to use N-methyldichloromaleimide (VI-1), R=Me, giving as the end product the compound (I-1) 2,6-dimethyl-1H,5H-[1,4]dithiino[2,3-c:5,6-c']dipyrrole-1,3,5,7(2H,6H)-tetrone.

If dichloromaleimide (VI-2), R=H is used as starting material, the compound (I-2) 1H,5H-[1,4]dithiino[2,3-c:5,6-c']dipyrrole-1,3,5,7(2H,6H)tetrone is obtained as end product.

As thiosulphate it is possible in principle to use all soluble inorganic thiosulphates, such as, for example, lithium thiosulphate, sodium thiosulphate, potassium thiosulphate, caesium thiosulphate, magnesium thiosulphate or ammonium thiosulphate. It is preferred to use sodium thiosulphate, potassium thiosulphate or ammonium thiosulphate, more preferably sodium thiosuiphate. It is of course also possible to use mixtures of these salts.

The terms "thiosulphate" and "thiosulphate salt" are also intended to encompass hydrates of these salts, where they exist.

The thiosulphate is used in amounts between 1.1 and 1.8 mol per mole of dichloromaleimide of the formula (VI). Preferred amounts are between 1.2 and 1.7 mol, more preferably between 1.3 and 1.6 mol of thiosulphate, per mole of dichloromaleimide of the formula (VI).

The thiosulphate can be added to the reaction mixture in solid form or as a solution, in water, for example. If appropriate, the thiosulphate can also be added in liquid form as a melt. Thus, for example, sodium thiosulphate pentahydrate melts at between 45° C. and 50° C. It is preferred to add the thiosulphate as a solution in water.

The reaction temperature in the process of the invention can be varied within wide limits and lies between 0° C. and 200° C. In order to obtain satisfactory space-time yields, it is preferred to operate at temperatures between 20° C. and 180° C., more preferably between 30° C. and 150° C.

The reaction time in the process of the invention is between 10 minutes and 24 hours. It is preferred to operate for between 30 minutes and 12 hours, more preferably between 1 and 6 hours.

Suitable solvents for the process of the invention include water, dimethyl sulphoxide, sulpholane, alcohols such as methanol, ethanol, propanol, isopropanol, butanol, tort-butanol, cyclopentanol, cyclohexanol, ethylene glycol and ethylene glycol monomethyl ether, esters such as methyl acetate and ethyl acetate, amides such as formamide, N,N-dimethylformamide, N,N-dimethylacetamide and N-methylpyrrolidone, ethers such as tetrahydrofuran and 1,4-dioxane, nitriles such as acetonitrile, propionitrile, butyronitrile and benzonitrile, ketones such as acetone, methyl ethyl ketone, methyl isobutyl ketone and pinacolone, or mixtures of these diluents.

It is preferred to use water, dimethyl sulphoxide, methanol, ethanol, propanol, isopropanol, butanol, tort-butanol, cyclohexanol, ethylene glycol, methyl acetate, N,N-dimethylformamide, N,N-dimethylacetamide, tetrahydrofuran, 1,4-dioxane, acetonitrile, acetone, methyl ethyl ketone, methyl isobutyl ketone, or mixtures of these diluents.

It is very preferred to use mixtures of water and methanol, ethanol, propanol, isopropanol, methyl acetate, tetrahydrofuran, 1,4-dioxane, acetonitrile or acetone.

The process of the invention is illustrated by, but not confined to, the following examples.

EXAMPLE 1

A solution of 90 g [0.5 mol] of N-methyldiehloromaleimide (VI-1) in 875 ml of methanol is introduced at room temperature and, over the course of about 10 minutes, a solution of 110.7 g [0.7 mol] of sodium thiosulfate in 188 ml of water is added dropwise, the internal temperature rising to 42° C. After the end of the addition, the temperature is raised to 60° C. and the mixture is stirred at this temperature for 4 hours. Thereafter the reaction mixture is cooled to 10° C., and the solid is isolated by filtration with suction, washed with three times 150 ml of water and then 100 ml of MeOH, and dried. This gives 53.7 g of green solid, which according to HPLC, analysis is composed to an extent of 98.4 area-% of the compound (I-1), corresponding to a yield of 74.9% of theory.

EXAMPLE 2

A solution of 18 g [0.1 mol] of N-methyldichloromaleimide (VI-1) in 100 ml of methanol is introduced at 65° C. and, over the course of about 10 minutes, a solution, likewise heated at 65° C., of 29.77 g [0.12 mol] of sodium thiosulfate pentahydrate in 100 ml of water is added dropwise. After the end of the addition, the mixture is stirred for 1 hour more at 65° C. Thereafter the reaction mixture is cooled to 15° C., 17 ml of water are added, and it is stirred for 15 minutes. Thereafter the solid is isolated by filtration with suction, washed with 70 ml of water and then 30 ml of MeOH, and dried. This gives 10.1 g of dark-green solid, which according to HPLC analysis is against reference material is composed to an extent of 97.76 percent by weight of the compound (I-1), corresponding to a yield of 70% of theory.

EXAMPLE 3

A solution of 18 g [0.1 mol] of N-methyldichloromaleimide (VI-1) in 100 ml of methanol is introduced at 65° C. and, over the course of about 10 minutes, a solution, likewise heated at 65° C., of 34.73 g [0.14 mol] of sodium thiosulfate pentahydrate in 100 ml of water is added dropwise. After the end of the addition, the mixture is stirred for 1 hour more at 65° C. Thereafter the reaction mixture is cooled to 15° C., 17 ml of water are added, and it is stirred for 15 minutes. Thereafter the solid is isolated by filtration with suction, washed with 70 ml of water and then 30 ml of MeGH, and dried. This gives 11.3 g of dark-green solid, which according to HPLC analysis against reference material is composed to an extent of 95.9 percent by, weight of the compound (I-1), corresponding to a yield of 76.8% of theory.

EXAMPLE 4

A solution of 18 g [0.1 mol] of N-methyldichloromaleimide (VI-1) in 100 ml of methanol is introduced at 65° C. and, over the course of about 10 minutes, a solution, likewise heated at 65° C., of 37.22 g [0.15 mol] of sodium thiosulfate pentahydrate in 100 ml of water is added dropwise. After the end of the addition, the mixture is stirred for 1 hour more at 65° C. Thereafter the reaction mixture is cooled to 15° C., 17 ml of water are added, and it is stirred for 15 minutes. Thereafter the solid is isolated by filtration with suction, washed with 70 ml of water and then 30 ml of MeOH, and dried. This gives 10.65 g of dark-green solid, which according to HPLC analysis against reference material is composed to an extent of 98 percent by weight of the compound (I-1), corresponding to a yield of 73.9% of theory.

EXAMPLE 5

A solution of 18 g [0.1 mol] of N-methyldichloromaleimide (VI-1) in 100 ml of methanol is introduced at 65° C. and, over the course of about 10 minutes, a solution, likewise heated at 65° C., of 39.7 g [0.16 mol] of sodium thiosulfate pentahydrate in 100 ml of water is added dropwise. After the end of the addition, the mixture is stirred for 1 hour more at 65° C. Thereafter the reaction mixture is cooled to 15° C., 17 ml of water are added, and it is stirred for 15 minutes. Thereafter the solid is isolated by filtration with suction, washed with 70 ml of water and then 30 ml of MeOH, and dried. This gives 10.4 g of dark-green solid, which according to HPLC analysis against reference material is composed to an extent of 97.3 percent by weight of the compound (I-1), corresponding to a yield of 71.7% of theory.

EXAMPLE 6

A solution of 360 g [2 mol] of N-methyldichloromaleimide (VI-1) in 3500 ml of methanol is introduced at room temperature and, over the course of about 20 minutes, a solution of 442.8 g [2.8 mol] of sodium thiosulfate in 750 ml of water is added dropwise. After the end of the addition, the temperature is raised to 60° C. and the mixture is stirred at this temperature for 4 hours. Thereafter the reaction mixture is cooled to 15° C., 250 ml of water are added, and it is stirred for 10 minutes. Thereafter the solid is isolated by filtration with suction, washed with 1200 ml of water and then 600 ml of MeOH, and dried. This gives 210.2 g of dark-green solid, which according to HPLC analysis against reference material is composed to an extent of 97.9 percent by weight of the compound (I-1), corresponding to a yield of 72.9% of theory.

EXAMPLE 7

A solution of 7.2 g [0.04 mol] of N-methyldichipromaleimide (VI-1) in 70 ml of methanol is introduced at room temperature and, over the course of about 10 minutes, a solution of 10.74 g [0.068 mol] of sodium thiosulfate in 23 ml of water is added dropwise. After the end of the addition, the temperature is raised to 60° C. and the mixture is stirred at this temperature for 4 hours. Thereafter the reaction mixture is cooled to 15° C., 10 ml of water are added, and it is stirred for 10 minutes. Thereafter the solid is isolated by filtration with suction, washed with 35 ml of water and then 10 ml of MeOH, and dried. This gives 3.83 g of green solid, which according HPLC analysis against reference material is composed to an extent of 94.7 percent by weight of the compound (I-1), corresponding to a yield of 64.2% of theory.

EXAMPLE 8

A solution of 7.2 g [0.04 mol] of N-methyldichloromaleimide (VI-1) in 70 ml of methanol is introduced at room temperature and, over the course of about 10 minutes, a solution of 12.64 g [0.08 mol] of sodium thiosulfate in 27 ml of water is added dropwise. After the end of the addition, the temperature is raised to 60° C. and the mixture is stirred at this temperature for 4 hours. Thereafter the reaction mixture is cooled to 15° C., 10 ml of water are added, and it is stirred for 10 minutes. Thereafter the solid is isolated by filtration with suction, washed with 35 ml of water and then 10 ml of MeOH, and dried. This gives 2.5 g of green solid, which according to HPLC analysis is composed to an extent of 83.7 area-% of the compound (I-1), corresponding to a yield of 37% of theory.

EXAMPLE 9

A solution of 18 g [0.1 mol] of N-methyldichloromaleimide (VI-1) in 100 ml of ethanol is introduced at 75° C. and, over the course of about 10 minutes, a solution, likewise heated at 75° C., of 34.73 g [0.14 mol] of sodium thiosulfate pentahydrate in 100 ml of water is added dropwise. After the end of the addition, the mixture is stirred for 1 hour more at 75° C. Thereafter the reaction mixture is cooled to 15° C., 17 ml of water are added, and it is stirred for 15 minutes. Thereafter the solid is isolated by filtration with suction, washed with 70 ml of water and then 30 ml of EtOH, and dried. This gives 11.0 g of dark-green solid, which according to HPLC analysis against reference material is composed to an extent of 97 percent by weight of the compound (I-1), corresponding to a yield of 75.5% of theory.

EXAMPLE 10

A solution of 7.2 g [0.04 mol] of N-methyldichloromaleimide (VI-1) in 70 ml of methanol is introduced at room temperature and, over the course of about 10 minutes, a solution of 6.52 g [0.044 mol] of ammonium thiosulfate in 15 ml of water is added dropwise. After the end of the addition, the temperature is raised to 45° C. and the mixture is stirred at 45° C. for 2 hours. Thereafter the reaction mixture is cooled to 10° C., stirred for 10 minutes more, and then the solid is isolated by filtration with suction, washed with 35 ml of water and then 10 ml of MeOH, and dried. This gives 3.50 g of dark-green solid, which according to HPLC analysis against reference material is composed to an extent of 97.1 percent by weight of the compound (I-1), corresponding to a yield of 60.2% of theory.

EXAMPLE 11

A solution of 7.2 g [0.04 mol] of N-methyldichloroinaleimide (VI-1) in 70 Ml of methanol is introduced at room temperature and, over the course of about 10 minutes, a solution of 8.3 g [0.056 mol] of ammonium thiosulfate in 15 ml of water is added dropwise. After the end of the addition, the temperature is raised to 45° C. and the mixture is stirred at 45° C. for 4 hours. Thereafter the reaction mixture is cooled to 10° C., stirred for 10 minutes more, and then the solid is isolated by filtration with suction, washed with 35 ml of water and then 10 ml of MeOH, and dried. This gives 3.85 g of dark-green solid, which according to HPLC analysis against reference material is composed to an extent of 983 percent by weight of the compound (I-1), corresponding to a yield of 67% of theory.

EXAMPLE 12

A solution of 6.64 g [0.04 mol] of dichloromaleimide (VI-2) in 40 ml of methanol is introduced at 65° C. and, over the course of about 10 minutes, a solution, likewise heated at 65° C., of 13.89 g [0.056 mol] of sodium thiosulfate pentahydrate in 40 ml of water is added dropwise. After the end of the addition, the mixture is stirred for hour more at 65° C. Thereafter the reaction mixture is cooled to 15° C., 10 and of water are added, and it is stirred for 15 minutes. Thereafter the solid is isolated by filtration with suction, washed with 30 ml of water and then 15 ml of MODEL and dried. This gives 3.6 g of dark-green solid, which according to HPLC analysis is composed to an extent of 99.6 area-% of the compound (I-2), corresponding to a yield of 71% of theory.

COMPARATIVE EXAMPLE 1

Corresponding to U.S. Pat. No. 3,364,229, Ex. IX; R=H

A solution of 18 g [0.1 mol] of N-methyldichloromaleimide (VI-1) in 100 ml of ethanol is introduced at 75° C. and, over the course of about 10 minutes, a solution, likewise heated at 75° C., of 24.8 g [0.10 mol] of sodium thiosulfate pentahydrate in 100 ml of water is added dropwise. After the end of the addition, the mixture is stirred for 1 hour more at 75° C. Thereafter the reaction mixture is cooled to 1.5° C., 17 ml of water are added, and it is stirred for 15 minutes. Thereafter the solid is isolated by filtration with suction, washed With 70 ml of water and then 30 ml of EtOH, and dried. This gives 9.1 g of dark-green solid, which according to HPLC analysis is composed to an extent of 94.3 area-% of the compound (I-1), corresponding to a yield of 60.8% of theory.

COMPARATIVE EXAMPLE 2

A solution of 18 g [0.1 mol] of N-methyldichloromaleimide (VI-1) in 100 ml of methanol is introduced at 65° C. and, over the course of about 10 minutes, a solution, likewise heated at 65° C., of 24.8 g [0.10 mol] of sodium thiosulfate pentahydrate in 100 ml of water is added dropwise. After the end of the addition, the mixture is stirred for 1 hour more at 65° C. Thereafter the reaction mixture is cooled to 15° C., 17 ml of water are added, and it is stirred for 15 minutes. Thereafter the solid is isolated by filtration with suction, washed With 70 ml of water and then 30 ml of MeOH, and dried. This gives 10.4 g of dark-green solid, which according to HPLC analysis against reference material is composed to an extent of 89.15 percent by weight of the compound (I-1), corresponding to a yield of 65.7% of theory.

General Data:

HPLC conditions: Zorbax Eclipse Plus C18 4.6*50 mm 1.8 µm, Eluent A: 0.1% $H_3PO_4$, Eluent B: acetonitrile, Gradient: 90/10, 20%/min. 5/95 (1.75), Flow rate: 2 ml/min, 55° C.

The invention claimed is:
1. A process for preparing a compound of formula (I)

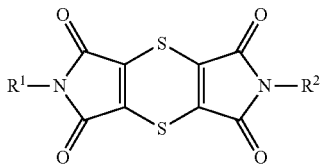

in which
R$^1$ and R$^2$ are identical or different and are hydrogen; C$_1$-C$_8$-alkyl which is optionally substituted with one or more halogen, —OR$^3$, or —COR$^4$; C$_3$-C$_7$-cycloalkyl which is optionally substituted with one or more halogen, C$_1$-C$_4$-alkyl, or C$_1$-C$_4$-haloalkyl; or aryl or aryl-(C$_1$-C$_4$-alkyl) each of which is optionally substituted with one or more halogen, C$_1$-C$_4$-alkyl, C$_1$-C$_4$-haloalkyl, —COR$^4$, or sulphonylamino,
R$^3$ is hydrogen, C$_1$-C$_4$-alkyl, C$_1$-C$_4$-alkylcarbonyl, or aryl, wherein the aryl is optionally substituted with one or more halogen, C$_1$-C$_4$-alkyl, or C$_1$-C$_4$-haloalkyl,
R$^4$ is hydroxyl, C$_1$-C$_4$-alkyl, or C$_1$-C$_4$-alkoxy,
comprising reacting
a compound of formula (VI)

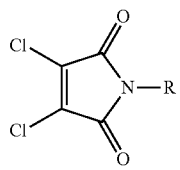

in which R is R$^1$ or R$^2$
with an inorganic thiosulphate in a solvent or solvent mixture, wherein between 1.3 and 1.6 moles of thiosulphate are used per mole of dichloromaleimide of formula (VI).

2. The process of claim 1, wherein the thiosulphate is soluble and is selected from lithium thiosulphate, sodium thiosulphate, potassium thiosulphate, cesium thiosulphate, magnesium thiosulphate, ammonium thiosulphate, or mixtures thereof.

3. The process of claim 1, wherein R$^1$ is hydrogen, methyl, ethyl, n-propyl, isopropyl, 2,2-difluoroethyl, 2,2,2-trifluoroethyl, cyclopropyl, or cyclohexyl.

4. The process of claim 1, wherein R$^1$ is hydrogen or methyl.

5. The process of claim 1, wherein the thiosulphate is selected from sodium thiosulphate, potassium thiosulphate, ammonium thiosulphate, or mixtures thereof.

6. The process of claim 1, wherein the thiosulfate is sodium thiosulfate.

7. The process of claim 1, wherein the solvent is selected from water, dimethyl sulphoxide, sulpholane, methanol, ethanol, propanol, isopropanol, butanol, tert-butanol, cyclopentanol, cyclohexanol, ethylene glycol, ethylene glycol monomethyl ether, methyl acetate, ethyl acetate, formamide, N,N-dimethylformamide, N,N-dimethylacetamide, N-methylpyrrolidone, tetrahydrofuran, 1,4-dioxane, acetonitrile, propionitrile, butyronitrile, benzonitrile, acetone, methyl ethyl ketone, methyl isobutyl ketone, pinacolone, or mixtures thereof.

8. The process of claim 1, wherein the solvent is selected from water, dimethyl sulphoxide, methanol, ethanol, propanol, isopropanol, butanol, tert-butanol, cyclopentanol, cyclohexanol, ethylene glycol, methyl acetate, N,N-dimethylformamide, N,N-dimethylacetamide, tetrahydrofuran, 1,4-dioxane, acetonitrile, acetone, methyl ethyl ketone, methyl isobutyl ketone, or mixtures thereof.

9. The process of claim 1, wherein the solvent is selected from water, methanol, ethanol, propanol, isopropanol, methyl acetate, tetrahydrofuran, 1,4-dioxane, acetonitrile, acetone, or mixtures thereof.

10. The process of claim 1, wherein the compound of formula (I) is 2,6-dimethyl-1H,5H-[1,4]dithiino[2,3-c:5,6-c']dipyrrole-1,3,5,7(2H,6H)tetrone or 1H,5H-[1,4]dithiino[2,3-c:5,6-c']dipyrrole-1,3,5,7(2H,6H)tetrone.

* * * * *